United States Patent
Vija et al.

(10) Patent No.: US 11,426,135 B2
(45) Date of Patent: Aug. 30, 2022

(54) MULTI-MODAL COMPTON AND SINGLE PHOTON EMISSION COMPUTED TOMOGRAPHY MEDICAL IMAGING SYSTEM

(71) Applicant: Siemens Medical Solutions USA, Inc., Malvern, PA (US)

(72) Inventors: Alexander Hans Vija, Evanston, IL (US); Miesher Rodrigues, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 38 days.

(21) Appl. No.: 17/250,543

(22) PCT Filed: Aug. 7, 2018

(86) PCT No.: PCT/US2018/045466
§ 371 (c)(1),
(2) Date: Feb. 2, 2021

(87) PCT Pub. No.: WO2020/032922
PCT Pub. Date: Feb. 13, 2020

(65) Prior Publication Data
US 2021/0282728 A1    Sep. 16, 2021

(51) Int. Cl.
*A61B 6/00* (2006.01)
*A61B 6/03* (2006.01)
(Continued)

(52) U.S. Cl.
CPC ............ *A61B 6/4417* (2013.01); *A61B 6/037* (2013.01); *A61B 6/4266* (2013.01);
(Continued)

(58) Field of Classification Search
None
See application file for complete search history.

(56) References Cited

U.S. PATENT DOCUMENTS

| 4,506,374 A | 3/1985 | Flynn |
| 4,529,882 A | 7/1985 | Lee |

(Continued)

FOREIGN PATENT DOCUMENTS

| EP | 2060932 B1 | 3/2017 |
| JP | 2004125757 A | 4/2004 |

(Continued)

OTHER PUBLICATIONS

Ordonez, Caesar E., Alexander Bolozdynya, and Wei Chang. "Doppler broadening of energy spectra in Compton cameras." Nuclear Science Symposium, 1997. IEEE. vol. 2. IEEE, 1997.
(Continued)

*Primary Examiner* — Hoon K Song

(57) ABSTRACT

A multi-modality imaging system allows for selectable photoelectric effect and/or Compton effect detection. The camera or detector is a module with a catcher detector. Depending on the use or design, a scatter detector and/or a coded physical aperture are positioned in front of the catcher detector relative to the patient space. For low energies, emissions passing through the scatter detector continue through the coded aperture to be detected by the catcher detector using the photoelectric effect. Alternatively, the scatter detector is not provided. For higher energies, some emissions scatter at the scatter detector, and resulting emissions from the scattering pass by or through the coded aperture to be detected at the catcher detector for detection using the Compton effect. Alternatively, the coded aperture is not provided. The same module may be used to detect using both the photoelectric and Compton effects where both the scatter detector and coded aperture are provided with the catcher detector. Multiple modules may be positioned together to form a larger camera, or a module is used alone. By using modules, any number of modules may be used to fit with a multi-modality imaging system. One or more such
(Continued)

modules may be added to another imaging system (e.g., CT or MR) for a multi-modality imaging system.

20 Claims, 8 Drawing Sheets

(51) Int. Cl.
   *G01N 23/20066* (2018.01)
   *G01R 33/48* (2006.01)

(52) U.S. Cl.
   CPC .......... *A61B 6/4275* (2013.01); *A61B 6/4411* (2013.01); *G01N 23/20066* (2013.01); *G01N 2223/063* (2013.01); *G01N 2223/50* (2013.01); *G01R 33/481* (2013.01)

(56) References Cited

U.S. PATENT DOCUMENTS

| | | | |
|---|---|---|---|
| 4,700,074 A | 10/1987 | Bosnjakovic | |
| 5,757,006 A | 5/1998 | DeVito et al. | |
| 5,821,541 A | 10/1998 | Turner | |
| 6,323,492 B1 | 11/2001 | Clinthome | |
| 6,346,706 B1 | 2/2002 | Rogers et al. | |
| 6,762,413 B2 | 7/2004 | Zeng | |
| 6,791,090 B2 | 9/2004 | Lin et al. | |
| 7,015,477 B2 | 3/2006 | Gunter | |
| 7,045,789 B2 | 5/2006 | Ogawa et al. | |
| 7,262,417 B2 | 8/2007 | Smith | |
| 7,291,841 B2 | 11/2007 | Nelson et al. | |
| 7,304,309 B2 | 12/2007 | Suhami | |
| 7,321,122 B2 | 1/2008 | Bryman | |
| 7,345,283 B2 | 3/2008 | Gunter | |
| 7,504,635 B2 | 3/2009 | Ramsden | |
| 7,550,738 B1 | 6/2009 | DeVito | |
| 7,573,039 B2 | 8/2009 | Smith | |
| 7,667,203 B2 | 2/2010 | Hindi et al. | |
| 7,831,024 B2 | 11/2010 | Metzler et al. | |
| 7,863,567 B1 | 1/2011 | Hynes et al. | |
| 7,928,399 B2 | 4/2011 | Myjak et al. | |
| 8,107,589 B2 | 1/2012 | Sakurai et al. | |
| 8,153,986 B2 | 4/2012 | Mihailescu et al. | |
| 8,217,362 B2 | 7/2012 | DeVito | |
| 8,299,437 B2 | 10/2012 | Nakamura | |
| 8,354,648 B2 | 1/2013 | Laurent et al. | |
| 8,476,595 B2 | 7/2013 | McKinsey et al. | |
| 8,515,011 B2 | 8/2013 | Mundy et al. | |
| 8,519,343 B1 | 8/2013 | Mihailescu et al. | |
| 8,716,669 B2 | 5/2014 | Miyaoka et al. | |
| 8,742,360 B2 | 6/2014 | Yamaguchi et al. | |
| 8,847,166 B2 | 9/2014 | Fukuchi et al. | |
| 9,606,245 B1 | 3/2017 | Czarnecki et al. | |
| 2002/0008205 A1 | 1/2002 | Kurfess et al. | |
| 2002/0134942 A1 | 9/2002 | Pehl et al. | |
| 2003/0161526 A1 | 8/2003 | Jupiter et al. | |
| 2004/0084624 A1 | 5/2004 | Meng et al. | |
| 2004/0251419 A1 | 12/2004 | Nelson et al. | |
| 2005/0139775 A1 | 6/2005 | Gono et al. | |
| 2005/0253073 A1 | 11/2005 | Joram et al. | |
| 2007/0253530 A1 | 11/2007 | Mihailescu et al. | |
| 2008/0088059 A1 | 4/2008 | Tang et al. | |
| 2008/0139914 A1 | 6/2008 | Gaved et al. | |
| 2009/0008565 A1 | 1/2009 | Gottesman | |
| 2009/0202041 A1 | 8/2009 | Shirahata et al. | |
| 2010/0001190 A1* | 1/2010 | Wieczorek | G01T 1/1642 250/363.04 |
| 2010/0090117 A1 | 4/2010 | Nelson | |
| 2010/0270462 A1 | 10/2010 | Nelson et al. | |
| 2010/0294945 A1 | 11/2010 | Cussonneau | |
| 2011/0303854 A1 | 12/2011 | DeVito | |
| 2012/0043467 A1 | 2/2012 | Gueorguiev et al. | |
| 2012/0132814 A1 | 5/2012 | Weinberg | |
| 2012/0217386 A1 | 8/2012 | Ricci et al. | |
| 2012/0290519 A1 | 11/2012 | Fontaine et al. | |
| 2014/0110592 A1 | 4/2014 | Nelson et al. | |
| 2014/0301535 A1 | 10/2014 | Williams et al. | |
| 2015/0331115 A1 | 11/2015 | Nelson et al. | |
| 2017/0012308 A1 | 1/2017 | Ikeuchi | |
| 2017/0322327 A1* | 11/2017 | Boardman | G01V 5/0016 |
| 2018/0172847 A1* | 6/2018 | Nelson | A61B 6/037 |
| 2018/0180747 A1* | 6/2018 | Matsuura | G01T 1/247 |

FOREIGN PATENT DOCUMENTS

| | | |
|---|---|---|
| JP | 2005514975 A | 5/2005 |
| JP | 2008522168 A | 6/2008 |
| JP | 2017522543 A | 8/2017 |
| WO | 2012058731 A1 | 5/2012 |

OTHER PUBLICATIONS

International Search Report for Corresponding International Application No. PCT/US2018/045466, dated Jun. 17, 2019.

* cited by examiner

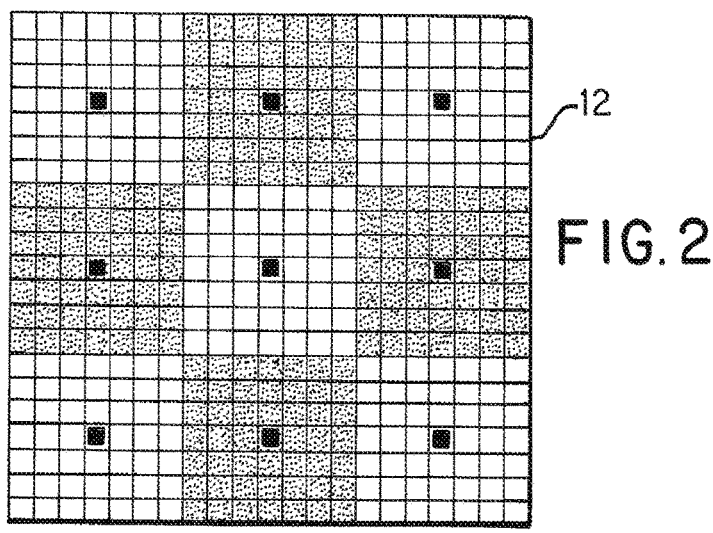
FIG. 2
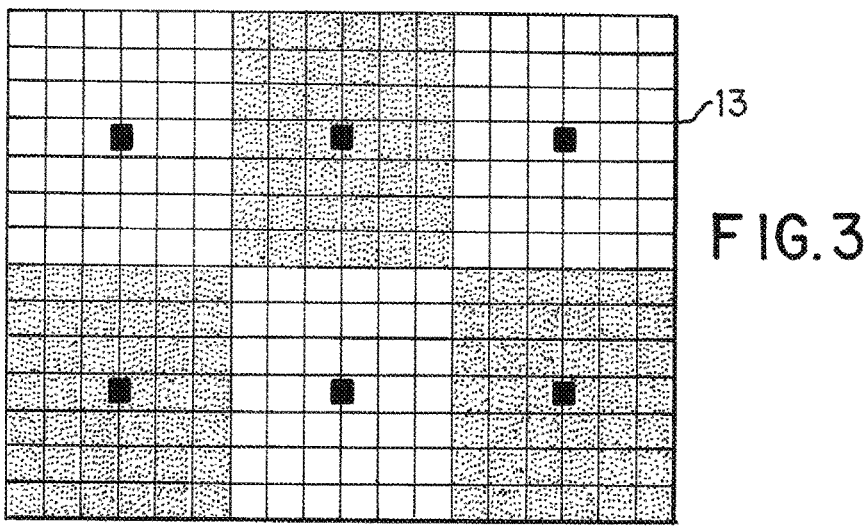
FIG. 3
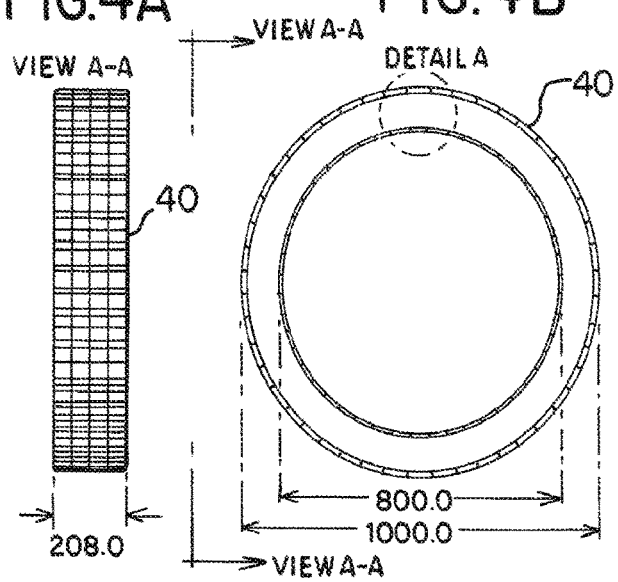 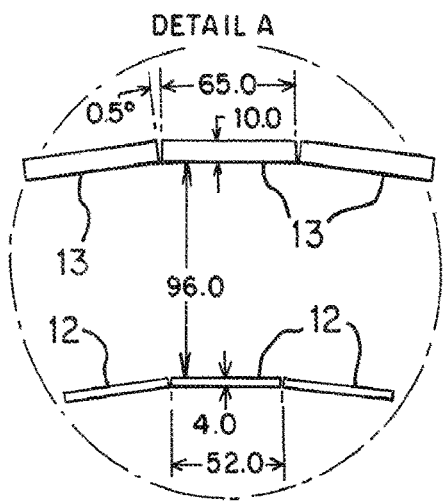
FIG. 4A  FIG. 4B  FIG. 4C

18 MODULES

34 MODULES

54 MODULES

MULTI-MODAL COMPTON AND SINGLE PHOTON EMISSION COMPUTED TOMOGRAPHY MEDICAL IMAGING SYSTEM

BACKGROUND

The present embodiments relate to nuclear imaging, such as single photon emission computed tomography (SPECT) imaging. Slowly rotating large field-of-view SPECT systems rely on the existence of a physical collimator. A parallel-hole collimator, which combined with a position-sensitive detector, forms the image. Relying on a photoelectric effect for detecting emissions from a radioisotope in the patient, these collimated SPECT systems are limited to low-energy photon emitting isotopes, such as Tc99m. Image quality and efficiency are key parameters of any image formation system for SPECT medical applications. Increased sensitivity and image quality are desirable features in new SPECT image formation systems as well as the added possibility of imaging higher photon energies.

The Compton effect allows for imaging higher energies. Compton imaging systems are constructed as test platforms, such as assembling a scatter ring and then a catcher ring mounted to a large framework. Electronics are connected to detect Compton-based events from emissions of a phantom. Compton imaging systems have failed to address design and constraint requirements for practical use in any commercial clinical settings. Current proposals lack the ability to be integrated into imaging platforms in the clinic or lack the design and constraint requirements (i.e., flexibility and scalability) to address commercial needs.

SUMMARY

By way of introduction, the preferred embodiments described below include methods and systems for medical imaging. A multi-modality imaging system allows for selectable photoelectric effect and/or Compton effect detection. The camera or detector is a module with a catcher detector. Depending on the use or design, a scatter detector and/or a coded physical aperture are positioned in front of the catcher detector relative to the patient space. For low energies, emissions passing through the scatter detector continue through the coded aperture to be detected by the catcher detector using the photoelectric effect. Alternatively, the scatter detector is not provided. For higher energies, some emissions scatter at the scatter detector, and resulting emissions from the scattering pass by or through the coded aperture to be detected at the catcher detector for detection using the Compton effect. Alternatively, the coded aperture is not provided. The same module may be used to detect using both the photoelectric and Compton effects where both the scatter detector and coded aperture are provided with the catcher detector. Multiple modules may be positioned together to form a larger camera or a module is used alone. By using modules, any number of modules may be used to fit with a multi-modality imaging system. One or more such modules may be added to another imaging system (e.g., CT or MR) for a multi-modality imaging system.

In a first aspect, multi-modality medical imaging system includes a first module having a first catcher detector, a position for a first scatter detector spaced from the catcher detector, and a position for a first physical aperture between a patient space and the first catcher detector. An image processor is configured to determine angles of incidence for Compton events where the first scatter detector is included in the first module and to count photoelectric events where the first physical aperture is included in the first module.

In a second aspect, a medical imaging system includes solid-state detector modules each with a first detector arranged to be used with either or both of a plate forming a coded aperture and a scatter detector. The solid-state detector modules having three, five, or six sides in a cross-section normal to a radial from longitudinal patient axis such that the solid-state detector modules stack together to form part of a geodesic dome.

In a third aspect, a method is provided for forming a Compton camera and/or a single photon emission computed tomography camera. A catcher detector is housed in a housing. The catcher detector arranged to be usable for relatively lower emission energies with a coded aperture and to be usable for relatively higher emission energies with a scatter detector. The housing is shaped as a part of a geodesic dome. The housing is mounted relative to a patient bed with a selected one or both of the coded aperture and the scatter detector.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 2 illustrates an example scatter detector;

FIG. 3 illustrates an example catcher detector;

FIG. 4A is a side view of one embodiment of a Compton camera, FIG. 4B is an end view of the Compton camera of FIG. 4A, and FIG. 4C is a detail view of a part of the Compton camera of FIG. 4B;

DETAILED DESCRIPTION OF THE DRAWINGS AND PRESENTLY PREFERRED EMBODIMENTS

Figure 1:
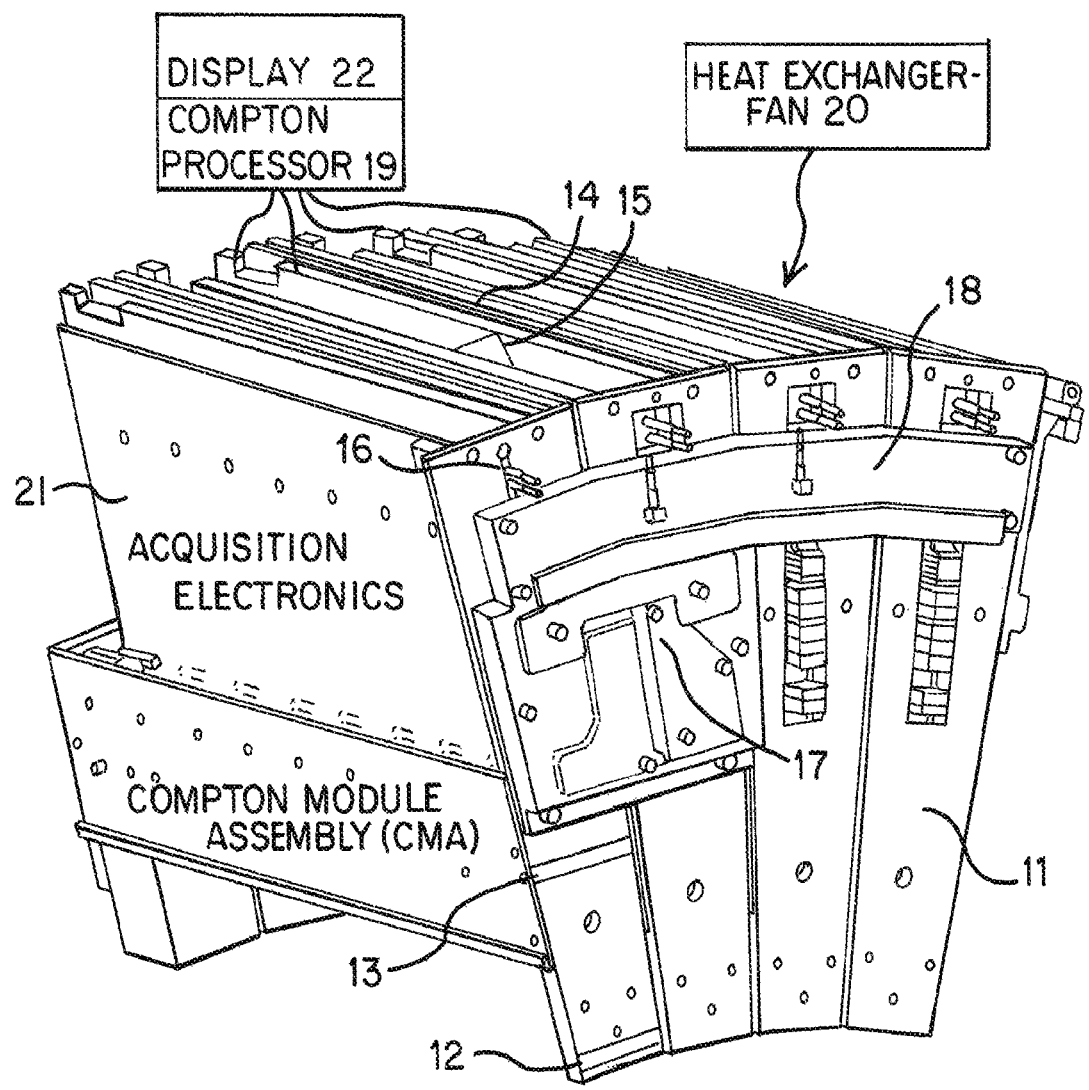
FIG. 1 is perspective view of multiple modules of a Compton camera according to one embodiment.

FIGS. 1-9 are directed to a multi-modality compatible Compton camera. A modular design is used to form the Compton camera for use with various other imaging modalities. FIGS. 11-16 are directed to a modular design with a catcher detector that may be used with either a scatter detector for Compton imaging or a coded aperture for SPECT imaging. The module provides positions for either or both of the scatter detector and coded aperture. After a summary of the selectable SPECT-Compton embodiments, the Compton camera of FIGS. 1-9 is described. Many of the features and components of the Compton camera of FIGS. 1-9 are used in the SPECT-Compton embodiments described in FIGS. 11-16.

For the selectable SPECT-Compton embodiments, a clinical multi-modality compatible and modular camera is provided for medical imaging. For lower energy emissions, a coded aperture may be included in each module for SPECT operation. For higher energy emissions, a scatter detector may be included in each module for Compton operation. The modular design allows enough flexibility that the selectable SPECT-Compton camera may be added to existing computed tomography (CT), magnetic resonance (MR), or positron emission tomography (PET) platforms, either as axially separated systems, or as fully integrated systems. Modularity allows efficient manufacturing and serviceability. Increased sensitivity and image quality are desirable features in new SPECT image formation systems as well as the added possibility of imaging higher photon energies. Hybrid imaging uses the Compton effect for higher energies and the photoelectric effect with physical collimation for low energies ~140.5 keV where both the scatter detector and coded aperture are provided in the respective positions of a same module.

Referring to FIGS. 1-9, a medical imaging system includes a multi-modality compatible Compton camera with segmented detection modules. The Compton camera, such as a Compton camera ring, is segmented into modules that house the detection units. Each module is independent, and when assembled into a ring or partial ring, the modules may communicate with each other. The modules are independent yet can be assembled into a multi-module unit that produces Compton scattering-based images. Cylindrically symmetric modules or spherical shell segmented modules may be used.

The scatter-catcher pair, modular arrangement allows efficient manufacturing, is serviceable in the field, and is cost and energy efficient. The modules allow for the design freedom to change the radius for each radial detection unit, angular span of one module, and/or axial span. The scatter-catcher pair modules are multi-modality compatible and/or form a modular ring Compton camera for clinical emission imaging. This design allows flexibility, so the Compton camera may be added to existing computed tomography (CT), magnetic resonance (MR), positron emission tomography (PET) or other medical imaging platforms, either as axially separated systems or as fully integrated systems. Each module may address heat dissipation, data collection, calibration, and/or allow for efficient assembly as well as servicing.

Each scatter-catcher paired module is formed from commercially suitable solid-state detector modules (e.g., Si, CZT, CdTe, HPGe or similar), allowing for an energy range of 100-3000 keV. Compton imaging may be provided with a wider range of isotope energies (>2 MeV), enabling new tracers/markers through selection of the scatter-catcher detectors. The modularity allows for individual module removal or replacement, allowing for time and cost-efficient service. The modules may be operated independently and isolated or may be linked for cross-talk, allowing for improved image quality and higher efficiency in detecting Compton events using a scatter detector of one module and a catcher detector of another module.

The modularity allows for flexible design geometry optimized to individual requirements, such as using a partial ring for integration with a CT system (e.g., connected between the x-ray source and detector), a few modules (e.g., tiling) used for integration with a single photon emission computed tomography gamma camera or other space limited imaging system, or a full ring. Functional imaging based on Compton-detected events may be added to other imaging systems (e.g., CT, MR, or PET). Multiple full or partial rings may be placed adjacent to each other for greater axial coverage of the Compton camera. A dedicated or stand-alone Compton-based imaging system may be formed. In one embodiment, the modules include a collimator for lower energies (e.g., <300 keV), providing for multichannel and multiplexed imaging (e.g., high energies using the scatter-catcher detectors for Compton events and low energies using one of the detectors for SPECT or PET imaging). The modules may be stationary or fast rotating (0.1 rpm<<$\omega$<<240 rpm). The dimensional, installation, service, and/or cost constraints are addressed by the scatter-catcher paired modules.

FIG. 1 shows one embodiment of modules 11 for a Compton camera. Four modules 11 are shown, but additional or fewer modules may be used. The Compton camera is formed from one or more modules, depending on the desired design of the Compton camera.

The Compton camera is for medical imaging. A space for a patient relative to the modules is provided so that the modules are positioned to detect photons emitted from the patient. A radiopharmaceutical in the patient includes a radio-isotope. A photon is emitted from the patient due to decay from the radio-isotope. The energy from the radio-isotope may be 100-3000 keV, depending on the material and structure of the detectors. Any of various radio-isotopes may be used for imaging a patient.

Each of the modules 11 includes the same or many of the same components. A scatter detector 12, a catcher detector 13, circuit boards 14, and baffle 15 are provided in a same housing 21. Additional, different, or fewer components may be provided. For example, the scatter detector 12 and catcher detector 13 are provided in the housing 21 without other components. As another example, a fiber optic data line 16 is provided in all or a sub-set of the modules 11.

The modules 11 are shaped for being stacked together. The modules 11 mate with each other, such as having matching indentation and extensions, latches, tongue-and-grooves, or clips. In other embodiments, flat or other surfaces are provided for resting against each other or a divider. Latches, clips, bolts, tongue-and-groove or other attachment mechanisms for attaching a module 11 to any adjacent modules 11 are provided. In other embodiments, the module 11 attaches to a gantry or other framework with or without direct connection to any adjacent modules 11.

The connection or connections to the other modules 11 or gantry may be releasable. The module 11 is connected and may be disconnected. The connection may be releasable, allowing removal of one module 11 or a group of modules 11 without removing all modules 11.

For forming a Compton camera from more than one module 11, the housing 21 and/or outer shape of the modules 11 is wedge shaped. The modules 11 may be stacked around an axis to form a ring or partial ring due to the wedge shape. The part closer to the axis has a width size that is narrower along a dimension perpendicular to the axis than a width size of a part further from the axis. In the modules 11 of FIG. 1, the housings 21 have the widest part furthest from the axis. In other embodiments, the widest part is closer to the axis but spaced away from the narrowest part closest to the axis. In the wedge shape, the scatter detector 12 is nearer to the narrower part of the wedge shape than the catcher detector 13. This wedge shape in cross-section along a plane normal to the axis allows stacking of the modules 11 in abutting positions, adjacently, and/or connected to form at least part of a ring about the axis.

The taper of the wedge provides for a number N of modules 11 to form a complete ring around the axis. Any number N may be used, such as N=10-30 modules. The number N may be configurable, such as using different housings 21 for different numbers N. The number of modules 11 used for a given Compton camera may vary, depending on the design of the Compton camera (e.g., partial ring). The wedge shape may be provided along other dimensions, such as having a wedge shape in a cross-section parallel to the axis.

The modules 11 as stacked are cylindrically symmetric as connected with a gantry of a medical imaging system. A narrowest end of the wedged cross-section is closest to a patient space of the medical imaging system and a widest end of the wedged cross-section may be furthest from the patient space. In alternative embodiments, other shapes than wedge allowing for stacking together to provide a ring or generally curved shape of the stack may be provided.

The housing 21 is metal, plastic, fiberglass, carbon (e.g., carbon fiber), and/or other material. In one embodiment, different parts of the housing 21 are of different materials. For example, tin is used for the housing around the circuit boards 14. Aluminum is used to hold the scatter detector 12 and/or catcher detector 13. In another example, the housing 12 is of the same material, such as aluminum.

The housing 21 may be formed from different structures, such as end plates having the wedge shape, sheets of ground plane housing the circuit boards 14, and separate structure for walls holding the scatter detector 12 and catcher detector 13 where the separate structure is formed of material through which photons of a desired energy from a Compton event may pass (e.g., aluminum or carbon fiber). In alternative embodiments, walls are not provided for the modules 11 between the end plates for a region where the scatter detector 12 and/or catcher detector 13 are positioned, avoiding interference of photons passing from the scatter detector 12 of one module 11 to a catcher detector 13 of another module 11. The housing 21 by and/or for holding the detectors 12, 13 is made of low attenuating material, such as aluminum or carbon fiber.

The housing 21 may seal the module or includes openings. For example, openings for air flow are provided, such as at a top of widest portion of the wedge shape at the circuit boards 14. The housing 21 may include holes, grooves, tongues, latches, clips, stand-offs, bumpers, or other structures for mounting, mating, and/or stacking.

Each of the solid-state detector modules 11 includes both scatter and catcher detectors 12, 13 of a Compton sensor. By stacking each module, the size of the Compton sensor is increased. A given module 11 itself may be a Compton sensor since both the scatter detector 12 and catcher detector 13 are included in the module.

The modules 11 may be separately removed and/or added to the Compton sensor. For a given module 11, the scatter detector 12 and/or catcher detector 13 may be removable from the module 11. For example, a module 11 is removed for service. A faulty one or both detectors 12, 13 are removed from the module 11 for replacement. Once replaced, the refurbished module 11 is placed back in the medical imaging system. Bolts, clips, latches, tongue-and-groove, or other releasable connectors may connect the detectors 12, 13 or part of the housing 21 for the detectors 12, 13 to the rest of the module 11.

The scatter detector 12 is a solid-state detector. Any material may be used, such as Si, CZT, CdTe, HPGe, and/or other material. The scatter detector 12 is created with wafer fabrication at any thickness, such as about 4 mm for CZT. Any size may be used, such as about 5×5 cm. FIG. 2 shows a square shape for the scatter detector 12. Other shapes than square may be used, such as rectangular. For the modules 11 of FIG. 1, the scatter detector 12 may be rectangular extending between two wedge-shaped end-plates.

In the module 11, the scatter detector 12 has any extent. For example, the scatter detector 12 extends from one wedge-shaped end wall to the other wedge-shaped end wall. Lesser or greater extent may be provided, such as extending between mountings within the module 11 or extending axially beyond one or both end-walls. In one embodiment, the scatter detector 12 is at, on, or by one end wall without extended to another end wall.

The scatter detector 12 forms an array of sensors. For example, the 5×5 cm scatter detector 12 of FIG. 2 is a 21×21 pixel array with a pixel pitch of about 2.2 mm. Other numbers of pixels, pixel pitch, and/or size of arrays may be used.

The scatter detector 12 includes semiconductor formatted for processing. For example, the scatter detector 12 includes an application specific integrated circuit (ASIC) for sensing photon interaction with an electron in the scatter detector 12. The ASIC is collocated with the pixels of the scatter detector 12. The ASIC is of any thickness. A plurality of ASICs may be provided, such as 9 ASICS in a 3×3 grid of the scatter detector 12.

The scatter detector 12 may operate at any count rate, such as >100 kcps/mm. Electricity is generated by a pixel due to the interaction. This electricity is sensed by the application specific integrated circuit. The location, time, and/or energy is sensed. The sensed signal may be conditioned, such as amplified, and sent to one or more of the circuit boards 14. A flexible circuit, wires, or other communications path carries the signals from the ASIC to the circuit board 14.

Compton sensing operates without collimation. Instead, a fixed relationship between energy, position, and angle of a photon interaction at the scatter detector 12 relative to a photon interaction at the catcher detector 13 is used to determine the angle of the photon entering the scatter detector 12. A Compton process is applied using the scatter detector 12 and the catcher detector 13.

The catcher detector 13 is a solid-state detector. Any material may be used, such as Si, CZT, CdTe, HPGe, and/or other material. The catcher detector 13 is created with wafer fabrication at any thickness, such as about 10 mm for CZT. Any size may be used, such as about 5×5 cm. The size may be larger along at least one dimension than the scatter detector 12 due to the wedge shape and spaced apart positions of the scatter detector 12 and the catcher detector 13. FIG. 3 shows a rectangular shape for the catcher detector 13 but other shapes may be used. For the modules 11 of FIG. 1, the catcher detector 13 may be rectangular extending between two end-plates where the length is the same as and the width is greater than the scatter detector 12.

The catcher detector 12 forms an array of sensors. For example, the 5×6 cm catcher detector 13 of FIG. 3 is a 14×18 pixel array with a pixel pitch of about 3.4 mm. The pixel size is larger than the pixel size of the scatter detector 12. The number of pixels is less than the number of pixels of the scatter detector 12. Other numbers of pixels, pixel pitch, and/or size of arrays may be used. Other relative pixels sizes and/or numbers of pixels may be used.

In the module 11, the catcher detector 13 has any extent. For example, the catcher detector 13 extends from one wedge-shaped end wall to the other wedge-shaped end wall. Lesser or greater extent may be provided, such as extending between mountings within the module 11 or extending axially beyond one or both end-walls. In one embodiment, the catcher detector 13 is at, on, or by one end wall without extending to another end wall.

The catcher detector 13 includes semiconductor formatted for processing. For example, the catcher detector 13 includes an ASIC for sensing photon interaction with an electron in the catcher detector 13. The ASIC is collocated with the pixels of the catcher detector 13. The ASIC is of any thickness. A plurality of ASICS may be provided, such as 6 ASICS in a 2×3 grid of the catcher detector 13.

The catcher detector 13 may operate at any count rate, such as >100 kcps/mm. Electricity is generated by a pixel due to the interaction. This electricity is sensed by the ASIC. The location, time, and/or energy is sensed. The sensed signal may be conditioned, such as amplified, and sent to one or more of the circuit boards 14. A flexible circuit, wires, or other communications path carries the signals from the ASIC to the circuit board 14.

The catcher detector 13 is spaced from the scatter detector 12 by any distance along a radial line from the axis or normal to the parallel scatter and catcher detectors 12, 13. In one embodiment, the separation is about 20 cm, but greater or lesser separation may be provided. The space between the catcher detector 13 and the scatter detector 12 is filled with air, other gas, and/or other material with low attenuation for photons at the desired energies.

The circuit boards 14 are printed circuit boards, but flexible circuits or other materials may be used. Any number of circuit boards 14 for each module may be used. For example, one circuit board 14 is provided for the scatter detector 12 and another circuit board 14 is provided for the catcher detector 13.

The circuit boards 14 are within the housing 21 but may extend beyond the housing 21. The housing 21 may be grounded, acting as a ground plane for the circuit boards 14. The circuit boards 14 are mounted in parallel with each other or are non-parallel, such as spreading apart in accordance with the wedge shape. The circuit boards are positioned generally orthogonal to the catcher detector 13. Generally is used to account for any spread due to the wedge shape. Brackets, bolts, screws, and/or stand-offs from each other and/or the housing 21 are used to hold the circuit boards 14 in place.

The circuit boards 14 connect to the ASICS of the scatter and catcher detectors 12, 13 through flexible circuits or wires. The ASICs output detected signals. The circuit boards 14 are acquisition electronics, which process the detected signals to provide parameters to the Compton processor 19. Any parameterization of the detected signals may be used. In one embodiment, the energy, arrival time, and position in three-dimensions is output. Other acquisition processing may be provided.

The circuit boards 14 output to each other, such as through a galvanic connection within a module 11, to the data bridge 17, and/or to a fiber optic data link 16. The fiber data link 16 is a fiber optic interface for converting electrical signals to optical signals. A fiber optic cable or cables provide the acquisition parameters for events detected by the scatter and catcher detectors 12, 13 to the Compton processor 19.

The data bridge 17 is a circuit board, wires, flexible circuit, and/or other material for galvanic connection to allow communications between modules 11. A housing or protective plate may cover the data bridge 17. The data bridge 17 releasably connects to one or more modules 11. For example, plugs or mated connectors of the data bridge 17 mate with corresponding plugs or mated connectors on the housing 21 and/or circuit boards 14. A latch, clip, tongue-and-groove, screw, and/or bolt connection may be used to releasably hold the data bridge 17 in place with the modules 11.

The data bridge 17 allows communications between the modules. For example, the fiber data link 16 is provided in one modules 11 and not another module 11. The cost of a fiber data link 16 in every module 11 is avoided. Instead, the parameters output by the other module 11 are provided via the data bridge 17 to the module 11 with the fiber data link 16. The circuit board or boards 14 of the module 11 with the fiber data link 16 route the parameter output to the fiber data link 16, using the fiber data link 16 to report detected events from more than one module 11. In alternative embodiments, each module 11 includes a fiber data link 16, so the data bridge 17 is not provided or communicates other information.

The data bridge 17 may connect other signals between the modules 11. For example, the data bridge 17 includes a conductor for power. Alternatively, a different bridge provides power to the modules 11 or the modules 11 are individually powered. As another example, clock and/or synchronization signals are communicated between modules 11 using the data bridge 17.

In the embodiment of FIG. 1, a separate clock and/or synchronization bridge 18 is provided. The clock and/or synchronization bridge 18 is a circuit board, wires, flexible circuit, and/or other material for galvanic connection to allow communication of clock and/or synchronization signals between modules 11. A housing or protective plate may cover the clock and/or synchronization bridge 18. The clock and/or synchronization bridge 18 releasably connects to one or more modules 11. For example, plugs or mated connectors of the clock and/or synchronization bridge 18 mate with corresponding plugs or mated connectors on the housing 21 and/or circuit boards 14. A latch, clip, tongue-and-groove, screw, and/or bolt connection may be used to releasably hold the clock and/or synchronization bridge 18 in place with the modules 11.

The clock and/or synchronization bridge 18 may connect with the same or different grouping of modules 11 as the data bridge 17. In the embodiment shown in FIG. 1, the data bridge 17 connects between pairs of modules 11 and the clock and/or synchronization bridge 18 connects over groups of four modules 11.

The clock and/or synchronization bridge 18 provides a common clock signal and/or synchronization signals for synchronizing clocks of the modules 11. One of the parameters formed by the circuit boards 14 of each module 11 is the time of detection of the event. Compton detection relies on pairs of events—a scatter event and a catcher event. Timing is used to pair events from the different detectors 12, 13. The common clocking and/or synchronization allows for accurate pairing where the pair of events are detected in different modules 11. In alternative embodiments, only scatter and catcher events detected in a same module 11 are used, so the clock and/or synchronization bridge 18 may not be provided.

Other links or bridges between different modules 11 may be provided. Since the bridges 17, 18 are removable, individual modules 11 may be removed for service while leaving remaining modules 11 in the gantry.

Each module 11 is air cooled. Holes may be provided for forcing air through the module 11 (i.e., entry and exit holes). One or more baffles 15 may be provided to guide the air within the module 11. Water, conductive transfer, and/or other cooling may be alternatively or additionally provided.

In one embodiment, the top portion of the wedge-shape module 11 or housing 21 is open (i.e., no cover on the side furthest from the patient area). One or more baffles 15 are provided along the centers of one or more circuit boards 14 and/or the housing 21. A fan and heat exchanger 20 force cooled or ambient temperature air into each module 11, such as along one half of the module 11 at a location spaced away from the catcher detector 13 (e.g., top of the module 11). The baffles 15 and/or circuit boards 14 guide at least some of the air to the airspace between the scatter detector 12 and the catcher detector 13. The air then passes by the baffles 15 and/or circuit boards 14 on another part (e.g., another half) of the module 11 for exiting to the heat exchanger 20. Other routing of the air may be provided.

The heat exchanger and fan 20 is provided for each individual module 11, so may be entirely or partly within the module 11. In other embodiments, ducting, baffles, or other structure route air to multiple modules 11. For example, groups of four modules 11 share a common heat exchanger and fan 20, which is mounted to the gantry or other framework for cooling the group of modules 11.

For forming a Compton sensor, one or more modules 11 are used. For example, two or more modules 11 are positioned relative to a patient bed or imaging space to detect photon emissions from the patient. An arrangement of a greater number of modules 11 may allow for detection of a greater number of emissions. By using the wedge shape, modules 11 may be positioned against, adjacent, and/or connected with each other to form an arc about the patient space. The arc may have any extent. The modules 11 directly contact each other or contact through spacers or the gantry with small separation (e.g., 10 cm or less) between the modules 11.

In one example, four modules 11 are positioned together, sharing a clock and/or synchronization bridge 18, one or more data bridges 17, and a heat exchanger and fan 20. One, two, or four fiber data links 16 are provided for the group of modules 11. Multiple such groups of modules 11 may be positioned apart or adjacent to each other for a same patient space.

Due to the modular approach, any number of modules 11 may be used. Manufacturing is more efficient and costly by building multiple of the same component despite use of any given module 11 in a different arrangement than used for others of the modules 11.

The fiber data links 16 of the modules 11 or groups of modules 11 connect to the Compton processor 19. The Compton processor 19 receives the values for the parameters for the different events. Using the energy and timing parameters, scatter and catcher events are paired. For each pair, the spatial locations and energies of the pair of events are used to find the angle of incidence of the photon on the scatter detector 12. The event pairs are limited to events in the same module 11 in one embodiment. In another embodiment, catcher events from the same or different modules 11 may be paired with scatter events from a given module 11. More than one Compton processor 19 may be used, such as for pairing events from different parts of a partial ring 40.

Once paired events are linked, the Compton processor 19 or another processor may perform computed tomography to reconstruct a distribution in two or three dimensions of the detected emissions. The angle or line of incidence for each event is used in the reconstruction.

Figure 5:
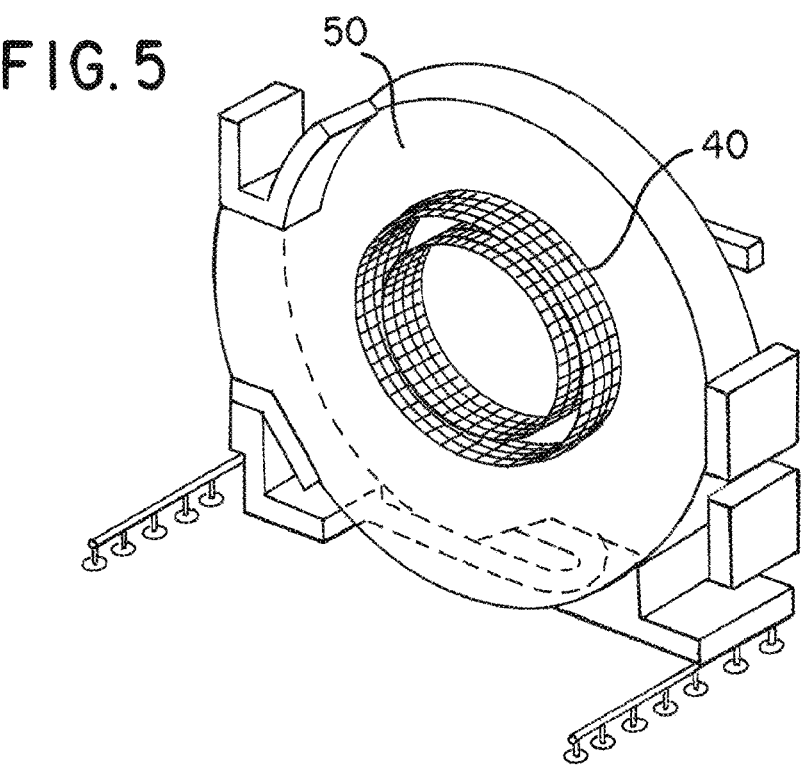
FIG. 5 is a perspective view of one embodiment of a Compton camera in a medical imaging system.
Figure 6:
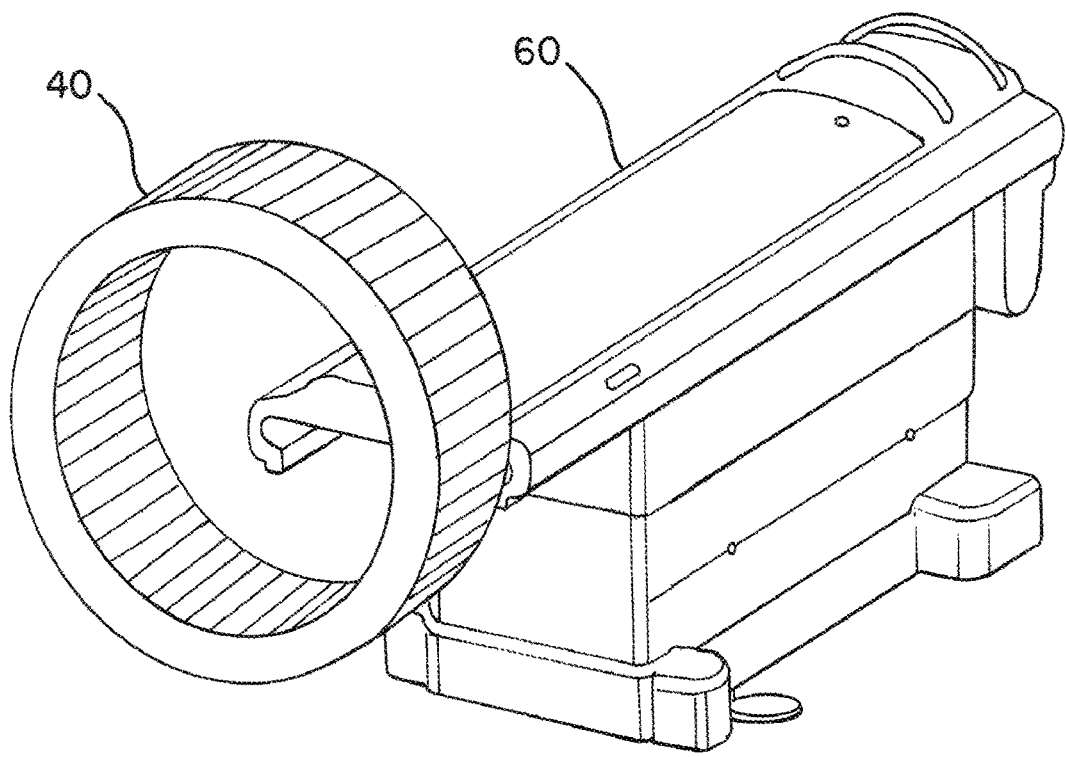
FIG. 6 is a perspective view of one embodiment of a full-ring Compton camera in a medical imaging system.

FIGS. 4A-6 shows one example arrangement of modules 11. The modules 11 form a ring 40 surrounding a patient space. FIG. 4A shows four such rings 40 stacked axially. FIG. 4B shows the scatter detectors 12 and corresponding catcher detectors 13 of the modules 11 in the ring 40. FIG. 4C shows a detail of a part of the ring 40. Three modules 11 provide corresponding pairs of scatter and catcher detectors 12, 13. Other dimensions than shown may be used. Any number of modules 11 may be used to form the ring 40. The ring 40 completely surrounds the patient space. Within a housing of a medical imaging system, the ring 40 connects with a gantry 50 or another framework as shown in FIG. 5. The ring 40 may be positioned to allow a patient bed 60 to move a patient into and/or through the ring 40. FIG. 6 shows an example of this configuration.

Figure 7:
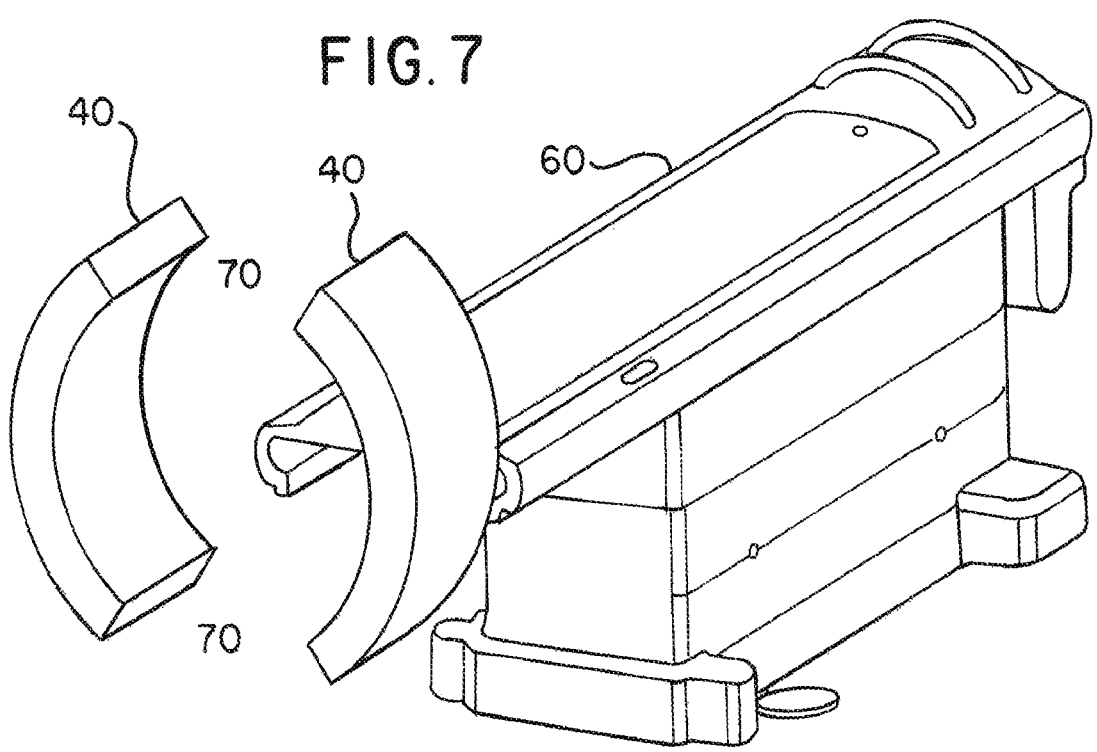
FIG. 7 is a perspective view of one embodiment of a partial-ring Compton camera in a medical imaging system.

The ring may be used for Compton-based imaging of emissions from a patient. FIG. 7 shows an example of using the same type of modules 11 but in a different configuration. A partial ring 40 is formed. One or more gaps 70 are provided in the ring 40. This may allow for other components to be used in the gaps and/or to make a less costly system by using fewer modules 11.

Figure 8:
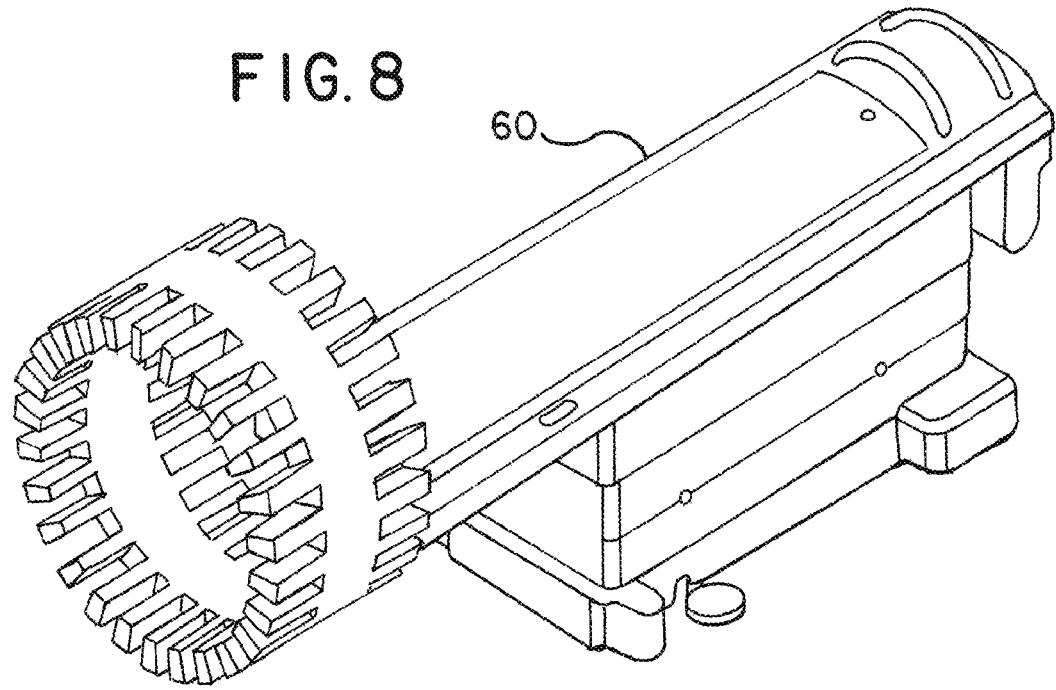
FIG. 8 is a perspective view of one embodiment of a full-ring Compton camera with partial-rings in axial extension in a medical imaging system.

FIG. 8 shows another configuration of modules 11. The ring 40 is a full ring. Additional partial rings 80 are stacked axially relative to the bed 60 or patient space, extending the axial extent of detected emissions. The partial rings 80 are in an every other or every group of N modules 11 (e.g., N=4) distribution rather than the two gaps 70 partial ring 40 of FIG. 7. The additional rings may be full rings. The full ring 40 may be a partial ring 80. The different rings 40 and/or partial rings 80 are stacked axially with no or little (e.g., less than ½ a module's 11 axial extent) apart. Wider spacing may be provided, such as having a gap of more than one module's 11 axial extent.

Figure 9:
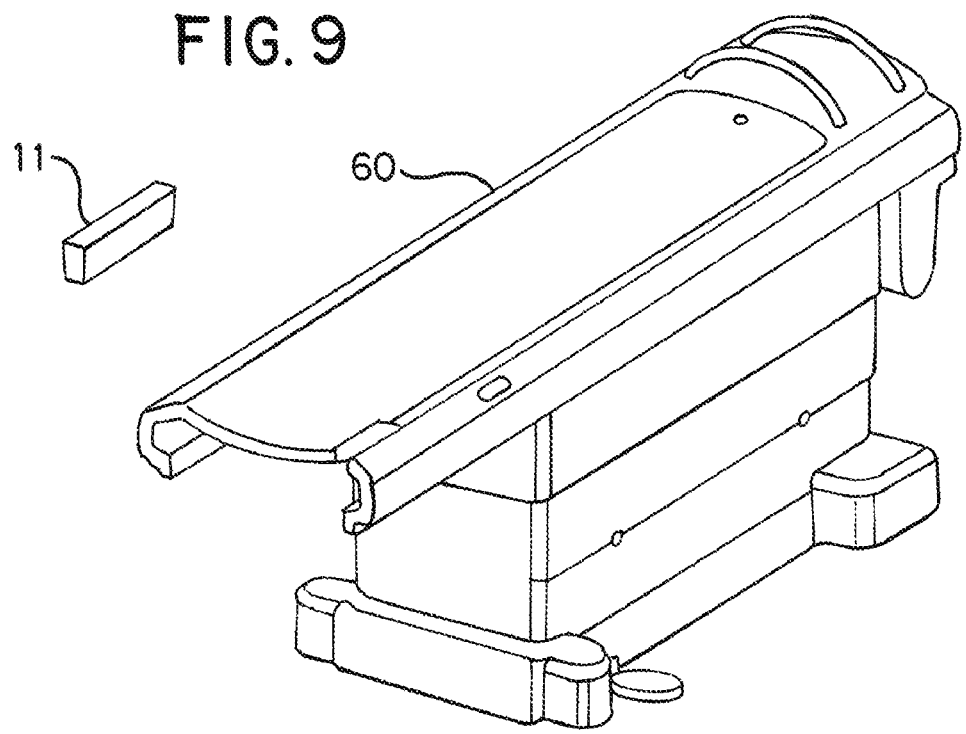
FIG. 9 is a perspective view of one embodiment of a single module-based Compton camera in a medical imaging system.

FIG. 9 shows yet another configuration of modules 11. One module 11 or a single group of modules 11 is positioned by the patient space or bed 60. Multiple spaced apart single modules 11 or groups (e.g., group of four) may be provided at different locations relative to the bed 60 and/or patient space.

In any of the configurations, the modules 11 are held in position by attachment to a gantry, gantries, and/or other framework. The hold is releasable, such as using bolts or screws. The desired number of modules 11 are used to assemble the desired configuration for a given medical imaging system. The gathered modules 11 are mounted in the medical imaging system, defining or relative to the patient space. The result is a Compton sensor for imaging the patient.

The bed 60 may move the patient to scan different parts of the patient at different times. Alternatively or additionally, the gantry 50 moves the modules 11 forming the Compton sensor. The gantry 50 translates axially along the patient space and/or rotates the Compton sensor around the patient space (i.e., rotating about the long axis of the bed 60 and/or patient). Other rotations and/or translations may be provided, such as rotating the modules 11 about an axis non-parallel to the long axis of the bed 60 or patient. Combinations of different translations and/or rotations may be provided.

The medical imaging system with the Compton sensor is used as a stand alone imaging system. Compton sensing is used to measure distribution of radiopharmaceutical in the patient. For example, the full ring 40, partial ring 40, and/or axially stacked rings 40, 80 are used as a Compton-based imaging system.

In other embodiments, the medical imaging system is a multi-modality imaging system. The Compton sensor formed by the modules 11 is one modality, and another modality is also provided. For example, the other modality is a single photon emission computed tomography (SPECT), a PET, a CT, or a MR imaging system. The full ring 40, partial ring 40, axially stacked rings 40,80, and/or singular module 11 or group of modules 11 are combined with the sensors for the other type of medical imaging. The Compton sensor may share a bed 60 with the other modality, such as being positioned along a long axis of the bed 60 where the bed positions the patient in the Compton sensor in one direction and in the other modality in the other direction.

The Compton sensor may share an outer housing with the other modality. For example, the full ring 40, partial ring 40, axially stacked rings 40,80, and/or singular module 11 or group of modules 11 are arranged within a same imaging system housing for the sensor or sensors of the other modality. The bed 60 positions the patient within the imaging system housing relative to the desired sensor. The Compton sensor may be positioned adjacent to the other sensors axially and/or in a gap at a same axial location. In one embodiment, the partial ring 40 is used in a computed tomography system. The gantry holding the x-ray source and the x-ray detector also holds the modules 11 of the partial ring 40. The x-ray source is in one gap 70, and the detector is in another gap 70. In another embodiment, the single module 11 or a sparse distribution of modules 11 connects with a gantry of a SPECT system. The module 11 is placed adjacent to the gamma camera, so the gantry of the gamma camera moves the module 11. Alternatively, a collimator may be positioned between the modules 11 and the patient or between the scatter and catcher detectors 12, 13, allowing the scatter and/or catcher detectors 12, 13 of the modules 11 to be used for photoelectric event detection for SPECT imaging instead of or in addition to detection of Compton events.

The module-based segmentation of the Compton sensor allows the same design of modules 11 to be used in any different configurations. Thus, a different number of modules 11, module position, and/or configuration of modules 11 may be used for different medical imaging systems. For example, one arrangement is provided for use with one type of CT system and a different arrangement (e.g., number and/or position of modules 11) is used for a different type of CT system.

The module-based segmentation of the Compton sensor allows for more efficient and costly servicing. Rather than replacing an entire Compton sensor, any module 11 may be disconnected and fixed or replaced. The modules 11 are individually connectable and disconnectable from each other and/or the gantry 50. Any bridges are removed, and then the module 11 is removed from the medical imaging system while the other modules 11 remain. It is cheaper to replace an individual module 11. The amount of time to service may be reduced. Individual components of a defective module 11 may be easily replaced, such as replacing a scatter or catcher detector 12, 13 while leaving the other. The modules 11 may be configured for operation with different radioisotopes (i.e., different energies) by using corresponding detectors 12, 13.

FIGS. 11-15 show embodiments where the modules 11 selectably include a physical aperture for SPECT detection using the photoelectric effect. The modules may selectably include a scatter detector for Compton detection. The modules may be used for both Compton detection and photoelectric detection. A multi-modality medical imaging system is formed from one or more of the modules. The arrangements and components of the modules 11 discussed for FIGS. 1-9 may be used for the modules 11 with the physical aperture.

The segmented detection modules 11 may be used to form a geodesic dome-like multi-layer multi-modal camera. The camera is segmented into modules that house the detection units. Each module 11 is independent, and when assembled into a ring, partial ring or other configuration, the modules 11 may communicate with each other. Each module 11 includes an inner shell-like layer, denominated scatter layer, and an outer shell-like layer, denominated catcher layer. Where multiple modulus 11 are used, the modules may at least partly surround the imaging object.

Figure 15:
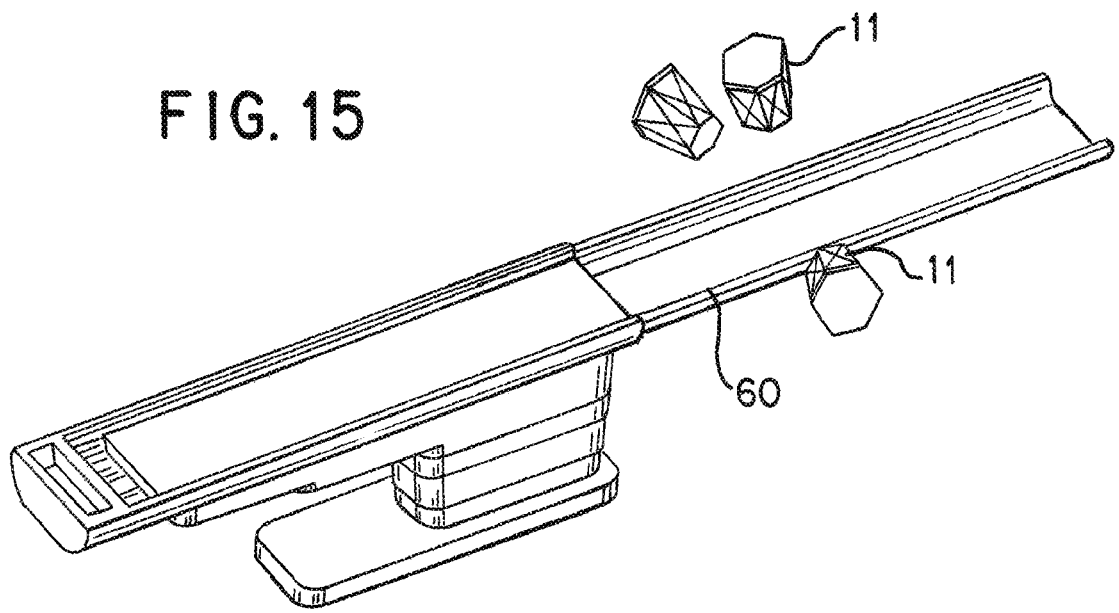
FIG. 15 is a perspective view of one embodiment of a multi-modality camera formed from three modules shaped for a geodesic dome-like structure.
Figure 16:
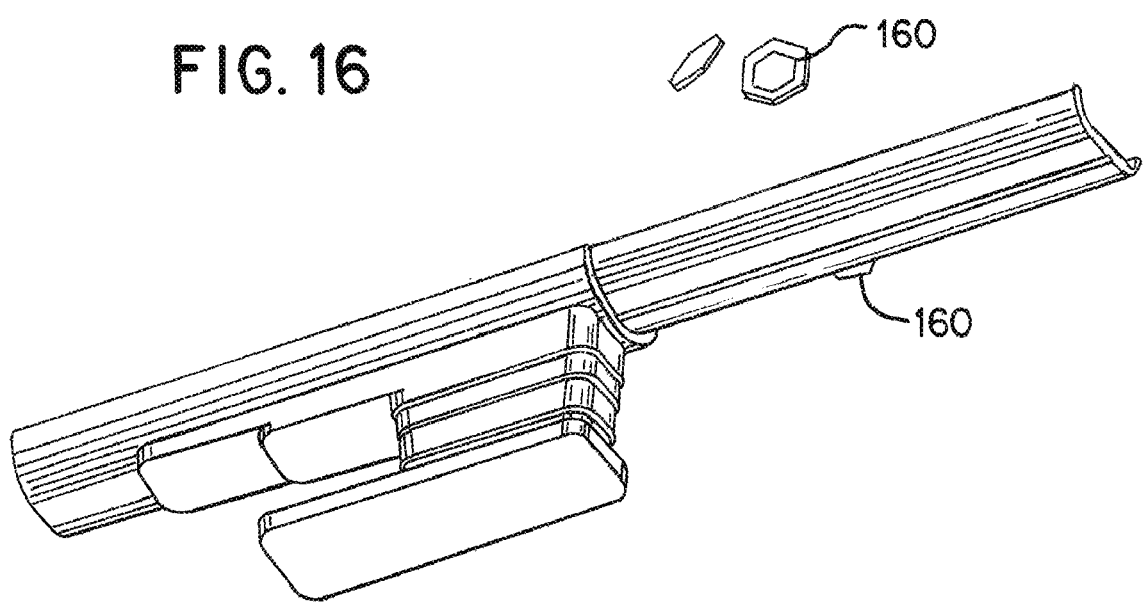
FIG. 16 is a perspective view of one embodiment of a photoelectric effect camera formed from three modules shaped for a geodesic dome-like structure.

FIG. 16 shows an embodiment of a medical imaging system where the modules 11 do not include the scatter detector, so provides for modular creation of a SPECT camera using the physical aperture and a detector. FIG. 15 shows an embodiment of a medical imaging system where the modules 11 include the scatter detector, so provides for modular creation of a Compton camera using the scatter detector. The modules 11 of FIG. 15 may include the physical aperture, so operate both as a Compton camera and a SPECT camera. Depending on the desired energies to be imaged for any given system, the base module with the catcher detector may be fitted with either or both of the scatter detector (e.g., higher energies) or the physical apertures (e.g., lower energies).

Figure 11:
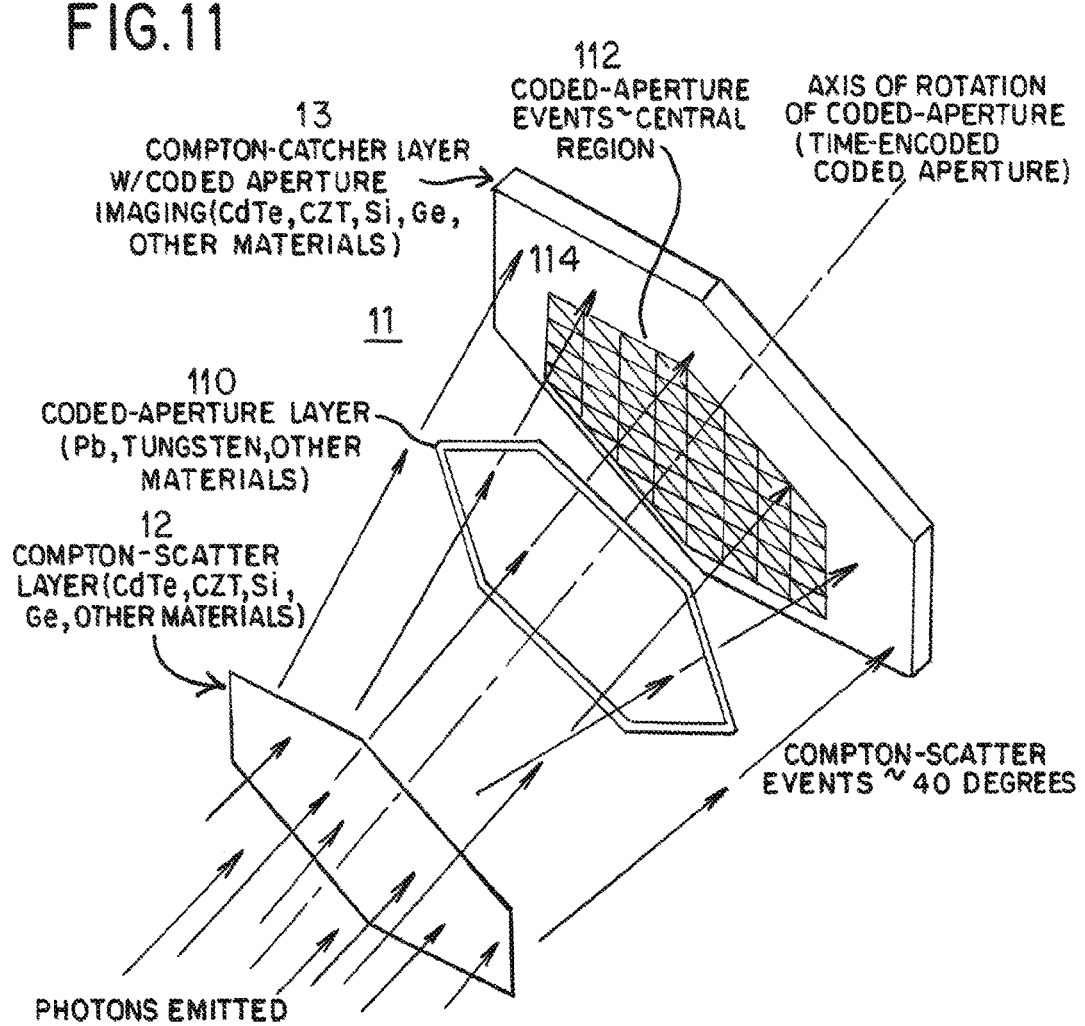
FIG. 11 illustrates the scatter and catcher detectors with an intervening coded aperture for imaging using both photoelectric and Compton effects.

FIG. 11 illustrates the detector structure of one module 11 where both the physical aperture 110 and the scatter detector 12 are selected and included in the same module 11. The module 11 includes the scatter detector 12 and the catcher detector 13. The scatter detector 12 and/or catcher detector 13 are solid-state detectors, so the module 11 is a solid-state detector module. A bracket, frame, clips, or other mechanical structure is provided for positioning the scatter detector 12 within the module 11 where the scatter detector 12 is selected to be included. The position may be at a given distance from the catcher detector 13 or may be adjustable in assembly or after assembled. Mechanical structures may be provided for positions of additional catcher and/or scatter detectors in the module 11 so that the designer of a given imaging system may select the number of catcher and/or scatter layers to include.

Additional catcher or scatter detectors 12, 13 may be provided, such as layering detectors 12, 13 in parallel normal to a radial from the patient space (e.g., along the axis of rotation in FIG. 11). Any emissions passing through one catcher detector 13 may interact in another catcher detector 13. Similarly, the intermediate detectors may operate as scatter detectors 12 due to an emission passing through the initial scatter detector 12. The intermediate detectors may have a same structure as either the scatter detector 12 or the catcher detector 13, but operate as scatter and/or catcher detectors 12, 13. One of the scatter detectors 12 generates Compton-scattering photons, which are captured by one of the sub-sequent catcher layers 13.

The modules 11 are independent yet may be assembled into a unit that produces multi-modal-based image formation images. The modules 11 allow for the design freedom in the shape to change radius for each radial detection unit, angular span of one module 11, and/or axial span. The dimensions and position of the modules 11 relative to a patient space may be altered in design as needed, such as by using a different housing.

Any of the shapes described for FIGS. 1-9 may be used. For example, FIG. 1 shows modules 11 with four sides in cross section orthogonal to a radial from the patient space. In one embodiment, the modules 11 have three, five, six, or more sides in cross section orthogonal to a radial from the patient space. FIG. 11 shows a six sided module 11. Where multiple modules 11 are to be used together, all the modules have a same number of sides. Alternatively, different modules 11 with a different number of sides are used together, such as a combination of modules 11 with five and six sides.

The three, five, or six sided modules have a narrower orthogonal cross section closer to the patient space than the orthogonal cross section further from the patient space, allowing for a geodesic dome. The modules 11 may be positioned to form a sphere or geodesic dome. For any given imaging system, a full dome is not used. Two or more modules 11 may be positioned to form part of a geodesic dome. In alternative embodiments, the modules 11 are not shaped for forming a sphere or geodesic dome, such as the modules 11 of FIG. 1 being shaped to form a ring or cylinder.

The modules 11 are cylindrically symmetric. A narrowest end of each of the modules 11 is closest to a patient space of the medical imaging system. A widest end of each of the modules 11 is further or furthest from the patient space. The scatter detector 12 is narrower and has less area than the catcher detector 13.

Where the modules 11 include both a scatter and catcher detectors 12, 13, Compton-based imaging may be provided. To detect events using the photoelectric effect for SPECT, a physical aperture 110 is included in the module 11. The physical aperture 110 is a plate or sheet of material. The physical aperture 110 is of any material that is opaque to lower energy (e.g., at about or less than 140.5 keV), such as lead or tungsten. Any thickness may be used, such as 0.5-5 mm (e.g., 1-3 mm). The thickness is chosen to allow all or some higher energy emissions or photons (e.g., >>140.5 keV) to pass for Compton detection.

The physical aperture 110 is positioned between the position for the scatter detector 12 and the catcher detector 13. Where intermediate detectors are provided, the physical aperture 110 may be between any of the detector layers. The coded aperture may be adjacent to the catcher detector 13, such as within 1 cm (e.g., within 5 mm), or spaced further from the catcher detector 13. In alternative embodiments, the physical aperture 110 is positioned in front of (i.e., closer to the patient space) of the position for the scatter detector 12.

A bracket, frame, clips, or other mechanical structure is provided for positioning the physical aperture 110 within the module 11 where the physical aperture 110 is selected to be included. The position may be at a given distance from the catcher detector 13 or may be adjustable in assembly or after assembled.

The physical aperture 110 is orthogonal to the radial from the patient space, so is parallel with the detectors 12, 13. Alternatively, the physical aperture 110 is not parallel with one or both detectors 12, 13 and/or is not orthogonal to the radial from the patient space. The radial is shown in FIG. 11 as an axis of rotation.

The physical aperture 110 has a same shape as the detectors 12, 13. For example and as shown in FIG. 11, the physical aperture 110 and detectors 12, 13 are six sided. The physical aperture 110 may have a different outer circumference shape than one or both detectors 12, 13.

The physical aperture 110 is a coded aperture. Holes in a regular or varying pattern are provided to cast a shadow on the catcher detector 13. The holes are of the same or different shapes and/or sizes. The holes are of sufficient size that emissions from different angles (e.g., 0-40 degrees away from orthogonal to the physical aperture 11) may pass through a hole. The coding in the holes of the aperture cause overlapping shadows on the catcher detector 13 as illuminated from a source (e.g., patient). The coding of the shadows may be used as a mask in reconstruction to deconvolve an image. In alternative embodiments, the physical aperture 110 is a parallel hole collimator (e.g., only emissions 0-1 degree from orthogonal pass through a hole).

To reduce noise, source size, and/or scattering problems, the coded aperture may be a time-encoded aperture. The physical aperture 110 rotates about a center axis (e.g., radial from the patient space). The coding in the shadow is shifted or changed for detecting at different times. Detections from different positions of the coded aperture 110 relative to the catcher detector 13 are used to reduce noise and/or distinguish background emissions from emissions from the patient. The time-encoded coded-aperture near the catcher detector 13 rotates around the axis of rotation to improve image quality and increase the field of view. In other embodiments, the physical aperture 110 translates instead or in addition to rotating. The translation shifts the position of the physical aperture 110 relative to the catcher detector 13 within the module 11. Other time encoding may be used.

In one embodiment, the physical aperture 110 is positioned relative to the catcher detector to cast the shadow on a center region 112 of the catcher detector 13 and not an outer region 114 of the catcher detector 13. For example, the physical aperture 110 has a same or similar (e.g., within 10%) area as the scatter detector 12 and a lesser area than the catcher detector 13. Due to scattering in Compton detection, the photons detected by the catcher layer for the Compton effect are more likely to be away from the center of the catcher detector 13. Conversely, since scattering is not used for the photoelectric effect, the photons detected using the photoelectric effect are more likely to be in the center region 112. The center region 112 records Compton scattered photons as well as photoelectric events that do not interact with inner detectors. The outer region 114 records only or mostly Compton scattered events from inner scatter detector 12 or other scatter detectors 12.

The actual structure of the catcher detector 13 may be uniform or the same for both the central region 112 and the outer region 114, but may have different pixel size, thickness, and/or other characteristics for the different regions 112, 114. The readings from the catcher detector 13 may be limited to one or both regions 112, 114 based on the type of imaging performed. Alternatively, different structure is used, or detection over the entire catcher detector 13 is used regardless of the type of imaging. Where modules 11 are arranged to communicate, Compton events from one module 11 may be detected with either region 112, 114 of another module 11.

The image processor 19 is configured to detect emissions with a photoelectric effect using the physical aperture 110 and the catcher detector 13 and to detect emissions with a Compton effect using the scatter detector 12 and the catcher detector 13. The detected events output by the circuit boards 14 are used by the image processor 19 for SPECT or Compton imaging. For SPECT, the coded or time-encoded aperture is used without events from the scatter detector 12. Photons at energies at about 140.5 keV or less are detected using the photoelectric effect. For Compton scatter, the scatter detector 12 and catcher detector 13 are used without the shadowing from the physical aperture 110. Photons at energies an order of magnitude larger (e.g., 1450 keV or larger) are detected using the Compton effect. The same modules 11 and image processor 19 are used for both photoelectric and Compton imaging.

For Compton detection, the events from the scatter and catcher detectors 12, 13 are paired and used to determine angles of incidence for Compton events in one or more modules 11. Photons may interact first in the scatter-layer(s) by Compton-scatter and then in the catcher-layer by photoelectric effect. These photons trigger both the scatter-layer(s) and the catcher-layer and deposit their full energy on all layers (multi-layer event). Due to scattering, over half or most of the events detected in the catcher detector 13 are in the outer region 114. The photon interaction events are primarily (over half or most) detected in the outer region 114. Compton reconstruction is used to determine the correct source direction by knowing (estimating) the Compton kinematics based on measured position (x,y,z) and energy (E) for paired events.

For photoelectric detection (i.e., SPECT imaging), photoelectric events from the catcher detector 13 are counted. The physical apertures 110 and catcher detectors 13 of the modules 11 are used. Photons may interact only in the catcher-layer by the photoelectric effect. The low energy photons may not trigger the scatter-layer and instead deposit their full energy on the catcher-layer (single-layer event). Since scattering is not used, the photoelectric events are counted from the center region 112 and not the outer region 114 of the catcher detector 13. Events from the outer region 114 may be used as measures of background.

A time-encoded coded-aperture may rotate around the axis of the module 11 and is used to determine the correct source direction. The time-encoded coded-aperture may reduce background (e.g., scatter, higher energy photons emitted by the source, etc.).

The image processor 19 is configured to generate a SPECT image. The counts and the positions on the catcher detector 13 (i.e., positions indicating the lines of response) are used to reconstruct a two or three-dimensional representation of the patient. The locations of emissions are represented. The image processor 19 is configured to generate a Compton image from the Compton events. A two or three-dimensional representation is reconstructed from the Compton scatter events and the corresponding estimated angles. For a three-dimensional representation of the object or image space, a two-dimensional image may be three-dimensionally rendered from the representation.

The display 22 is a CRT, LCD, projector, printer, or other display. The display 22 is configured to display the SPECT image and/or the Compton image. The image or images are stored in a display plane buffer and read out to the display 22. The images may be displayed separately or are combined, such as displaying the Compton image overlaid with or adjacent to the SPECT image.

FIGS. 12-16 show medical imaging systems formed from two or more modules 11. The shape of the solid-state detector modules 11 allow the modules 11 to stack together with or without direct contact to form part of a geodesic dome. The modules 11 may be combined to form a 3D geodesic dome-like SPECT-Compton camera. FIGS. 12-16 show different realizations of the same concept having 18, 34, 54, 3 and 3, modules respectively.

Figure 12:
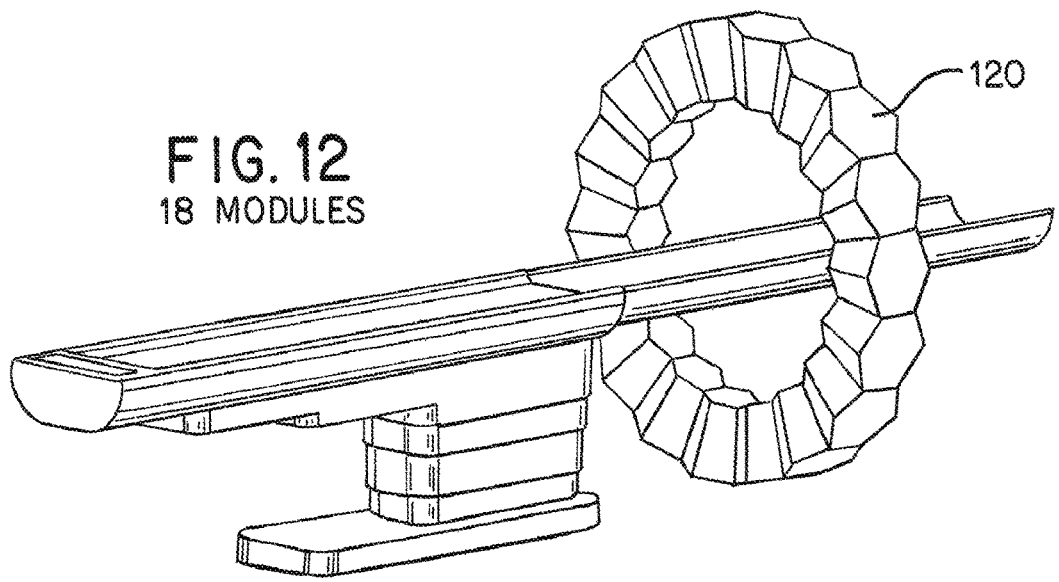
FIG. 12 is a perspective view of one embodiment of a full-ring multi-modality camera from modules shaped for a geodesic dome-like structure.

FIG. 12 shows the modules 11 used to form a full ring 120. Based on the radius of the ring and size of the modules 11, eighteen modules 11 form the full ring 120. More or fewer modules 11 may be used to form the full ring 120. One or more partial rings may be formed instead.

Figure 13:
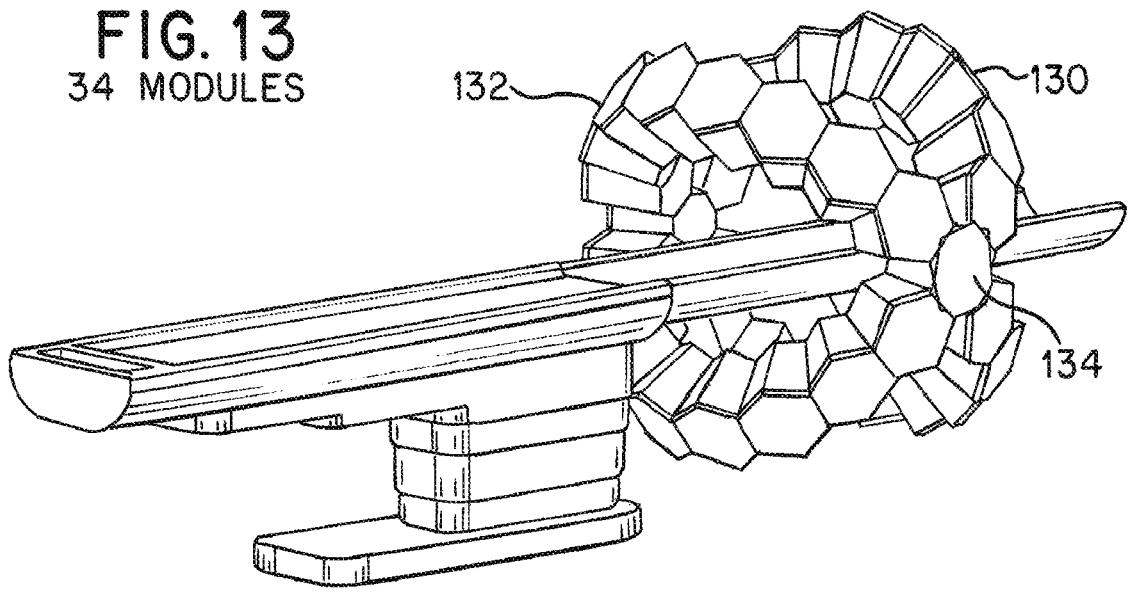
FIG. 13 is a perspective view of one embodiment of a dual-ring multi-modality camera from modules shaped for a geodesic dome-like structure.

FIG. 13 shows the modules 11 used to form two full rings 130, 132. The two rings 130, 132 intersect, so share two of the modules 134. One of the rings 130 is at 90 degrees to the other ring 132. Depending on the number of sides and/or the shape of the modules 134, other angles may be provided. In the example of FIG. 13, thirty-four modules 11 form the two rings 130, 132. Other numbers of modules 11 may be used. One or both rings 130, 132 may be partial rings. The rings 130, 132 are separate but intersect. In other embodiments, the rings 130, 132 do not intersect and are spaced from each other in parallel or non-parallel planes. Additional rings may be included.

The rings 130, 132 are held in place or stationary. In other embodiments, the rings 130, 132 connect to hinges or a rotary axis. The rings 130, 132 pivot about a common axis, such as an axis through the two shared modules 134. Translation and/or rotation of both rings 130, 132 or each ring 130, 132 independently may be provided.

Figure 14:
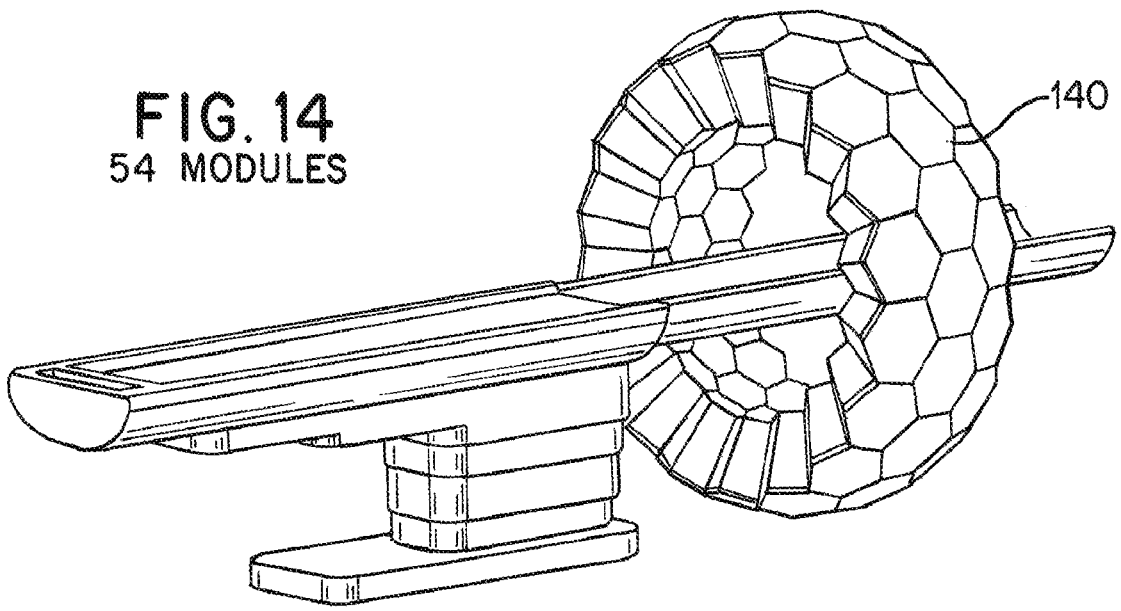
FIG. 14 is a perspective view of one embodiment of multiple full-rings stacked axially in a multi-modality camera from modules shaped for a geodesic dome-like structure.

FIG. 14 shows the modules 11 used to form three rings into a larger part of a geodesic dome 140 as compared to FIGS. 12 and 13. Part of a spherical shell is formed from the segmented modules 11. The three rings are axially adjacent to each other with little (e.g., less than ½ width of a module 11) or no separation. The rings may be in direct contact with each other and/or mounted to a same gantry or framework. Three full rings are shown, but one or more rings may be partial rings. Two, four, or more rings may be used. In the example of FIG. 14, fifty-four modules 11 are used for the three rings, but additional or fewer number of modules 11 may be used.

FIG. 15 shows three modules 11 positioned relative to the patient bed 60. One, two, four, or more modules 11 may be used. The modules 11 are spaced from each other by one or more module widths, but lesser separation or adjacent placement may be used. The modules 11 may be connected with another modality, such as a dedicated SPECT camera. The modules 11 connect with a gantry to allow rotation around and/or translation (e.g., transaxially) along a patient. Alternatively or additionally, the bed 60 moves the patient relative to the modules 11.

FIG. 16 shows the three-module arrangement of FIG. 15 using a different type of module 160. The scatter detector 12 is removed, allowing the modules 160 to be less high or have a smaller extent along the radial from the patient space. The same height may be used, such as using the same housings but without the scatter detector 12. Compton imaging is not provided, so the modules 160 use the physical aperture 110 with one or more catcher detectors 13. The catcher detector 13 functions with the time encoded coded aperture 110 for SPECT or photoelectric effect-based imaging. The catcher detector 13 absorbs photons by the photoelectric effect. The time encoded coded-aperture 110 near the catcher layer may rotate around the axis of rotation to improve image quality. The coded aperture may also move in the XY detector plane (sideways) to increase the field of view. Other arrangements of the modules 160 for SPECT imaging may be used, such as the arrangements of FIGS. 12-14. A single module 160 may be used. Less or more modules built in any of different configurations may be used.

Figure 10:
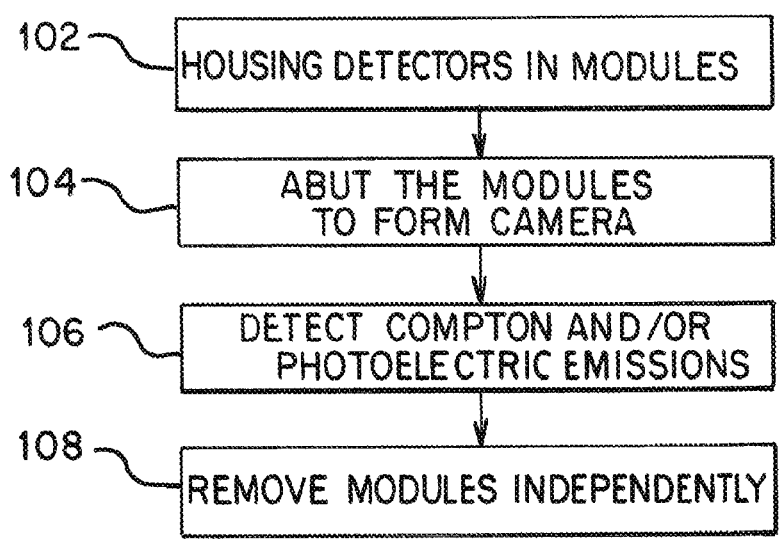
FIG. 10 is a flow chart diagram of an example embodiment of a method for forming a Compton camera.

FIG. 10 shows one embodiment of a flow chart of a method for forming, using, and repairing a camera selectable to be a Compton camera, a SPECT camera, or both. The camera is formed in a segmented approach. Rather than hand assembling the entire camera in place, one or more catcher detectors are positioned relative to each other to form a desired configuration of the camera. The catcher detectors are arranged to be usable for relatively lower emission energies with a coded aperture and to be usable for relatively higher emission energies with a scatter detector. This selectable and segmented approach may allow different configurations using the same parts, ease of assembly, ease of repair, and/or integration with other imaging modalities.

Other embodiments form a combination of a Compton camera and a SPECT camera where both the scatter detector and coded apertures are selected to be used in a same camera with the catcher detector. The segmented module 11 of FIG. 11 is used. The modules 160 of FIG. 16 may be used for forming a SPECT camera without the scatter detector being included. The modules 11 of FIG. 11 may be used for forming a Compton camera without the coded apertures.

The method may be implemented by the system of FIG. 1 to assemble a Compton sensor as shown in any of FIGS. 4-9. The method may be implemented by the system of FIG. 11 to assemble a Compton sensor as shown in any of FIGS. 12-16. Other systems, modules, and/or configured Compton sensors may be used.

The acts are performed in the order shown (i.e., top to bottom or numerically) or other orders. For example, act 108 may be performed as part of act 104.

Additional, different, or fewer acts may be provided. For example, acts 102 and 104 are provided for assembling the Compton camera without performing acts 106 and 108. As another example, act 106 is performed without other acts.

In act 102, catcher detectors are housed in separate housings. Modules are assembled where each module includes a catcher detector. A machine and/or person manufactures the housings. Only one housing and corresponding module may be used.

The modules are shaped to abut where the scatter and catcher detector pairs of different ones of the housings are non-planar. For example, a wedge shape and/or positioning is provided so that the detector pairs from an arc, such as shown in FIG. 4C. The shape allows and/or forces the arc shape when the modules are positioned against one another.

For the Compton-SPECT camera (e.g., FIG. 11), the scatter detector, coded aperture, and catcher detector are housed in a housing. The housings and corresponding modules have any shape, such as being shaped to be part of or form part of a geodesic dome. The housing selectably includes one or both of the scatter detector and the coded aperture. Depending on the design and/or emission energy requirements, the same housing with positions for both the scatter detector and the coded aperture may be used even where only one of the scatter detector or coded aperture are positioned or installed. Alternatively, different housings are used depending on which of the scatter detector and/or coded aperture are to be included.

In act 104, the housings are abutted. A person or machine assembles the Compton sensor from the housings. By stacking the housings adjacent to each other with direct contact or contact through spacers, gantry, or framework, the abutted housings form the arc. A full ring or partial ring is formed around and at least in part defines a patient space. Based on the design of the Compton camera, SPECT camera, or Compton-SPECT camera, any number of housings with the corresponding scatter and catcher detector pairs are positioned together to form a camera. A single housing may be used.

The housings may be abutted as part of a multi-modality system or to create a single imaging system. For a multi-modality system, the housings are positioned in a same outer housing and/or relative to a same bed as the sensors for the other modality, such as SPECT, PET, CT, or MR imaging system. The same or different gantry or support framework may be used for the housings of the Compton camera and the sensors for the other modality. For the embodiments of FIGS. 11-15, the modules provide the multi-modality by providing for both a Compton camera and the SPECT imaging system.

The configuration or design of the Compton camera defines the number and/or position of the housings. Once abutted, the housings may be connected for communications, such as through one or more bridges. The housings may be connected with other components, such as an air cooling system and/or a Compton processor.

In act 106, the assembled Compton camera detects emissions. A given emitted photon interacts with the scatter detector. The result is scattering of another photon at a particular angle from the line of incidence of the emitted photon. This secondary photon has a lesser energy. The secondary photon is detected by the catcher detector. Based on the energy and timing of both the detected scatter event and catcher event, the events are paired. The positions and energies for the paired events provides a line between the detectors and an angle of scattering. As a result, the line of incidence of the emitted photon is determined.

To increase the likelihood of detecting the secondary photon, the catcher events from one housing may be paired with the scatter events of another housing. Due to the angles, scatter from one scatter detector may be incident on the paired catcher detector in the same housing or a catcher detector in another housing. By the housings being open in the detector region and/or using low photon attenuating materials, a greater number of Compton events may be detected.

The detected events are counted or collected. The lines of response or lines along which the different Compton events occur are used in reconstruction. The distribution in three dimensions of the emissions from the patient may be reconstructed based on the Compton sensing. The reconstruction does not need a collimator as the Compton sensing accounts for or provides the angle in incidence of the emitted photon.

Using the Compton-SPECT modules 11 of FIG. 11, the modules may also be used to detect emissions as photoelectric events. The lower energy emissions pass through the scatter detector. These emissions may pass through holes in the coded aperture or are blocked by the coded aperture. The catcher detector detects at least some of the emissions passing through the holes of the coded aperture. Depending on the selection to include either or both of the scatter detector and coded aperture, emissions at relatively lower and/or higher energies are detected.

The detected events are used to reconstruct the locations of the radioisotope. Compton and/or photoelectric images are generated from the detected events and corresponding line information from the events.

In act 108, a person or machine (e.g., robot) removes one of the housings. When one of the detectors or associated electronics of a housing fails or is to be replaced for detecting at different energies, the housing may be removed. The other housings are left in the medical imaging system. This allows for easier repair and/or replacement of the housing and/or detectors without the cost of a greater disassembly and/or replacement of the entire Compton camera.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A multi-modality medical imaging system comprising:
a first module having a first catcher detector, a position for a first scatter detector spaced from the catcher detector, and a position for a first physical aperture between a patient space and the first catcher detector; and
an image processor configured to determine angles of incidence for Compton events where the first scatter detector is included in the first module and to count photoelectric events where the first physical aperture is included in the first module.

2. The multi-modality medical imaging system of claim 1 wherein the first physical aperture is at the position of the first physical aperture and the first physical aperture comprises a coded aperture of lead or tungsten.

3. The multi-modality medical imaging system of claim 2 wherein the coded aperture comprises a time-encoded aperture rotatable about an axis and/or translatable in a plane perpendicular to the axis to cast shadows with different positions on the first catcher detector.

4. The multi-modality medical imaging system of claim 1 wherein the first physical aperture is at the position of the first physical aperture and the first catcher detector and the first physical aperture are parallel, the first physical aperture having a shadow on the first catcher detector in a center region of the first catcher detector and not an outer region of the first catcher detector, and wherein the image processor is configured to count the photoelectric events from the center region and not the outer region and to determine the angles of incidence for the Compton events with photon interaction events primarily from the outer region.

5. The multi-modality medical imaging system of claim 1 further comprising a second module having a second catcher detector with positions for a second scatter detector and a second physical aperture; and
wherein the first and second modules are three, five, or six sided in cross-section orthogonal to a radial from a patient space.

6. The multi-modality medical imaging system of claim 5 wherein the first and second modules are cylindrically symmetric, a narrowest end of each of the first and second modules being closest to a patient space of the medical imaging system, a widest end of each of the first and second modules being furthest from the patient space.

7. The multi-modality medical imaging system of claim 1 wherein the first module further comprises circuit boards orthogonal to the first catcher detector, application specific integrated circuits with the first catcher detector, flexible circuits connecting the application specific integrated circuits to the circuit boards, and positions for one or more additional catcher and/or scatter layers between the first catcher layer and the first scatter layer.

8. The multi-modality medical imaging system of claim 1 wherein the first module is part of a ring or partial ring around a patient space of the medical imaging system.

9. The multi-modality medical imaging system of claim 8 further comprising additional modules for the ring or partial ring and for another ring or partial ring intersecting with the ring or partial ring at two of the additional modules.

10. The multi-modality medical imaging system of claim 9 wherein the ring or partial ring and the other ring or partial ring are 90 degrees apart.

11. The multi-modality medical imaging system of claim 8 further comprising an additional ring or partial ring of modules axially adjacent to the ring or partial ring with the first module, the additional ring or partial ring and the ring or partial ring forming part of a geodesic dome.

12. The multi-modality medical imaging system of claim 1 wherein the first scatter detector is at the position of the first scatter detector in the module, the first physical aperture is at the position of the first physical aperture in the module, and wherein the image processor is configured to generate a single photon emission computed tomography image from the count and a Compton image from the Compton events, and further comprising a display configured to display the single photon emission computed tomography image and the Compton image.

13. The multi-modality medical imaging system of claim 1 wherein the first scatter detector is included in the first module at the position for the first scatter detector where relatively higher energies are to be detected and wherein the first physical aperture is included in the first module at the position for the first physical aperture where relatively lower energies are to be detected.

14. A medical imaging system comprising:
solid-state detector modules each with a first detector arranged to be used with either or both of a plate forming a coded aperture and a scatter detector;
the solid-state detector modules having three, five, or six sides in a cross-section normal to a radial from longitudinal patient axis such that the solid-state detector modules stack together to form part of a geodesic dome.

15. The medical imaging system of claim 14 wherein each of the solid-state detector modules further comprises the scatter detector and the plate, the plate being between the scatter detector and the first detector, further comprising an image processor configured to detect emissions with a photoelectric effect using the plate and the first detector and to detect emissions with a Compton effect using the scatter detector and the first detector.

16. The medical imaging system of claim 14 wherein each of the solid-state detector modules includes the plate, the plate being rotatable and/or translatable relative to the first detector within the respective solid-state detector modules.

17. The medical imaging system of claim 14 wherein the stack to form the part of the geodesic dome comprises two separate rings sharing two of the solid-state modules.

18. A method for forming a Compton camera and/or a single photon emission computed tomography camera, the method comprising:
- housing a catcher detector in a housing, the catcher detector arranged to be usable for relatively lower emission energies with a coded aperture and to be usable for relatively higher emission energies with a scatter detector, the housing shaped as a part of a geodesic dome; and
- mounting the housing relative to a patient bed with a selected one or both of the coded aperture and the scatter detector.

19. The method of claim 18 wherein mounting comprises forming a ring or partial ring with the housing and additional ones of the housing as part of a multi-modality system including the Compton camera using the scatter detector in the housing and a single photon emission computed tomography imaging system using the coded aperture in the housing.

20. The method of claim 18 further comprising:
- detecting a first emission as a Compton event with the scatter detector and the catcher detector; and
- detecting a second emission as a photoelectric event passing through the coded aperture with the catcher detector.

* * * * *